(12) United States Patent
Peterson

(10) Patent No.: US 6,450,982 B1
(45) Date of Patent: Sep. 17, 2002

(54) CINCH CLIP FOR CAST OR BANDAGE PROTECTOR

(76) Inventor: Lloyd E. Peterson, 13205 Lakeview Dr., Burnsville, MN (US) 55337

(*) Notice: Subject to any disclaimer, the term of this patent is extended or adjusted under 35 U.S.C. 154(b) by 0 days.

(21) Appl. No.: 09/932,637

(22) Filed: Aug. 17, 2001

(51) Int. Cl.[7] .................................................. A61F 5/00
(52) U.S. Cl. ............................... 602/3; 24/18; 24/130; 24/129 B
(58) Field of Search ................................. 602/3, 60–62; 24/300, 17 B, 130, 18, 129 B; 36/8.1, 2 R; 2/239, 16, 59; 128/846, 849

(56) References Cited

U.S. PATENT DOCUMENTS

| | | | |
|---|---|---|---|
| 547,000 A | * | 10/1895 | Dean ......................... 24/115 R |
| 949,716 A | | 2/1910 | Quenzer |
| 1,424,803 A | * | 8/1922 | Corbett ............................ 24/18 |
| 3,747,125 A | * | 7/1973 | Goldman et al. ............... 2/240 |
| 4,215,687 A | | 8/1980 | Shaw |
| 4,254,765 A | | 3/1981 | Brown et al. |
| 4,363,317 A | | 12/1982 | Broucek |
| 4,414,969 A | | 11/1983 | Heyman |
| 4,422,455 A | | 12/1983 | Olsen |
| 4,523,586 A | | 6/1985 | Couri |
| 4,530,350 A | * | 7/1985 | Brown et al. ................... 602/3 |
| 4,562,834 A | | 1/1986 | Bates et al. |
| 4,727,864 A | | 3/1988 | Wiesenthal et al. |
| 4,911,151 A | | 3/1990 | Rankin et al. |
| 5,111,807 A | | 5/1992 | Spahn et al. |
| 5,555,607 A | * | 9/1996 | Parveris ..................... 24/239 R |
| 5,671,509 A | * | 9/1997 | Yeung ........................... 24/130 |
| 5,791,022 A | * | 8/1998 | Bohman ........................ 24/130 |
| 5,817,038 A | * | 10/1998 | Orange et al. .................. 602/3 |
| 5,882,320 A | * | 3/1999 | Peterson ......................... 602/3 |
| 5,979,028 A | * | 11/1999 | Hicks et al. ................ 24/712.9 |
| 6,119,318 A | * | 9/2000 | Maurer .......................... 24/130 |

* cited by examiner

Primary Examiner—Denise M. Pothier
Assistant Examiner—Quang D Thanh
(74) Attorney, Agent, or Firm—James W. Miller

(57) ABSTRACT

A cast or bandage protector comprises a lightweight, plastic bag that is open at one end. The user can insert an arm or leg through the open end of the bag to protect a cast or bandage from getting wet. A cinch clip is looped around the open end of the bag and can be tightened to cinch the open end of the bag closed. The cinch clip comprises a cord having a first end fixed to a locking member attached to the bag. The other end of the cord passes through an opening in the locking member after the cord is first looped around the user's arm or leg. If the second end of the cord is pulled to cinch the cord tight, the cord may be locked in this cinched condition by pulling the cord down into a tapered slot in the locking member to grip and hold the cord. The second end of the cord can include a handle to allow the cord to be more easily gripped and pulled. The cord is preferably an elastic cord.

19 Claims, 3 Drawing Sheets

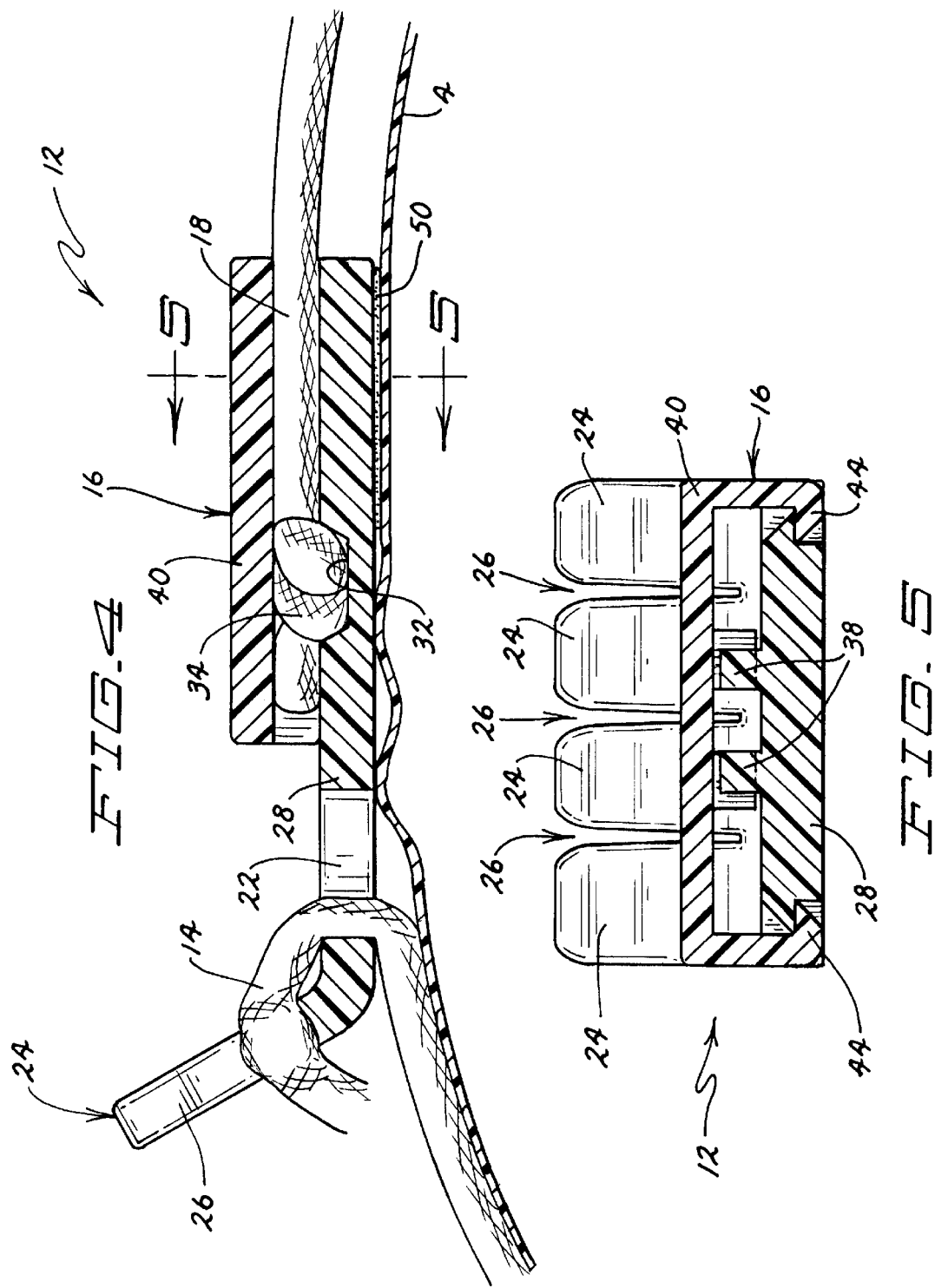

CINCH CLIP FOR CAST OR BANDAGE PROTECTOR

TECHNICAL FIELD

This invention relates to a cinch clip for closing the mouth of a cast or bandage protector to seal the cast or bandage protector around the user's limb, such as an arm or leg, and to hold the cast or bandage protector on the user's limb. This invention also relates to a cast or bandage protector having such a cinch clip.

BACKGROUND OF THE INVENTION

Cast or bandage protectors are known which comprise elongated bags that fit around the arm or leg of a user to cover a cast or bandage that has been applied to the arm or leg. The protector prevents the cast or bandage from getting wet. As such, it is used primarily when the user is bathing in a bath or shower. However, it is not limited to that use, but could also be worn while the user is outside to prevent rain from reaching the cast or bandage.

Certain protectors of the prior art comprise bags that are closed at one end and open at the other end. A strap is attached to the bag near the open end of the bag. The strap carries a buckle at one end. The other end of the strap is free to be inserted through the buckle.

In using these protectors, the user inserts whatever limb has the cast or bandage into the bag until the cast or bandage is located within the bag. The user then threads the free end of the strap through the buckle and pulls back on the free end of the strap to cinch the strap tight. The free end of the strap is then secured in place. My own U.S. Pat. No. 5,882,320 shows a cast or bandage protector of this type.

While prior cast protectors are effective, the bags must be tightly sealed around the user's limb, both to exclude water from the interior of the bag and to keep the bag in place. If the user does not pull the strap tightly enough, this need will not be met. Yet, if the strap is pulled and cinched very tightly, the cast protector can be uncomfortable, particularly since known straps used in prior art cast protectors are made from a non-extensible fabric or plastic. Thus, the need to have a tightly secured protector conflicts to some degree with the desire to provide a protector that is comfortable when in place. This conflict has not been satisfactorily resolved by cast or bandage protectors in the prior art.

SUMMARY OF THE INVENTION

One aspect of this invention relates to a cinch clip for cinching an item tightly to a limb of a user. The cinch clip comprises a locking member attached to the item during use of the cinch clip. A cord has a first end fixedly attached to the locking member and a free second end that is threaded through an opening in the locking member with the cord forming a loop relative to the locking member between the first and second ends thereof. At least one slot is provided on the locking member for releasably gripping the cord after the second end of the cord has been pulled through the opening to tighten the cord loop around the limb of the user to thereby cinch and tighten the item to the limb of the user.

Another aspect of this invention relates to a cinch clip for cinching an item tightly to a limb of a user. The cinch clip comprises a locking member attached to the item during use of the cinch clip. A cord has a first end fixedly attached to the locking member and a second free second end that is releasably attachable to the locking member to cinch the cord tightly around the limb of the user. The cord is an elastic cord.

Yet another aspect of this invention relates to a cast or bandage protector for covering an arm or leg of a user that utilizes the above-described cinch clip. The cast or bandage protector comprises an elongated, flexible, plastic bag having an open end into which the arm or leg of the user can be inserted until the arm or leg is contained at least partly within the bag. The cinch clip is carried adjacent the open end of the bag for cinching the open end of the bag shut against the arm or leg of the user.

BRIEF DESCRIPTION OF THE DRAWINGS

This invention will be described more completely in the following Detailed Description, when taken in conjunction with the following drawings, in which like reference numerals refer to like elements throughout.

FIG. 4 is a cross-sectional view of the cinch clip shown in FIG. 1 taken on lines 4—4 in FIG. 2, particularly illustrating use of the cinch clip on the exterior of a cast or bandage protector; and FIG. 5 is a cross-sectional view of a portion of the cinch clip shown in FIG. 1 taken on lines 5—5 in FIG. 4.

DETAILED DESCRIPTION

Figure 1:
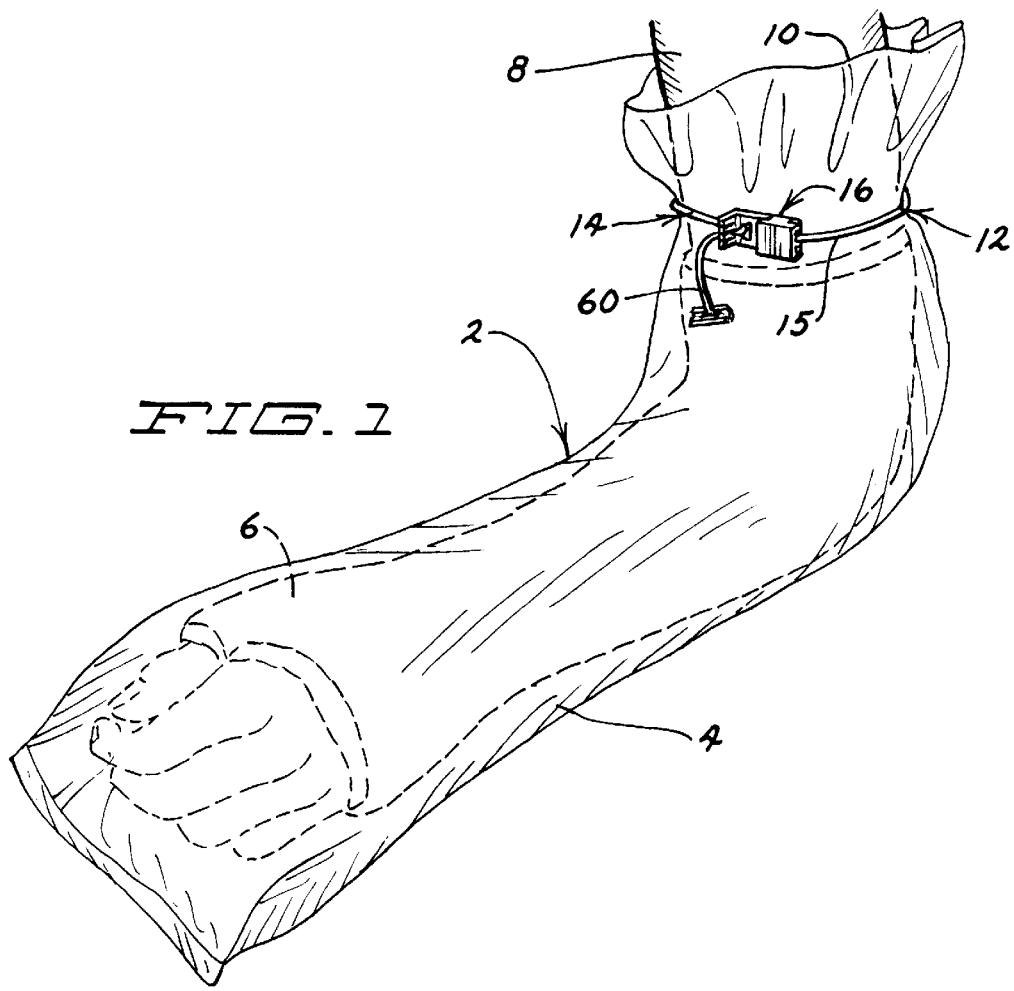
FIG. 1 is a perspective view of a cast or bandage protector secured around a cast or bandage on a user's arm by the cinch clip of this invention.

FIG. 1 shows a generally conventional cast or bandage protector 2 in the form of a flexible plastic bag 4 covering a cast or bandage 6 on the arm 8 of a user. One end of bag 4 has an open mouth 10 to allow bag 4 to be slipped over the user's arm 8 with the remainder of bag 4 being closed. This invention relates to a cast or bandage protector 2 having a cinch clip 12 for cinching mouth 10 of bag 4 tightly around the user's arm 8. This serves a dual purpose, namely to both hold bag 4 in place and to prevent water from leaking into bag 4 while the user is taking a shower or bathing.

This invention also relates to cinch clip 12 per se since cinch clip 12 can be used for cinching or securing other items around or to the limbs of a user, as will be explained in more detail hereafter.

Figure 2:
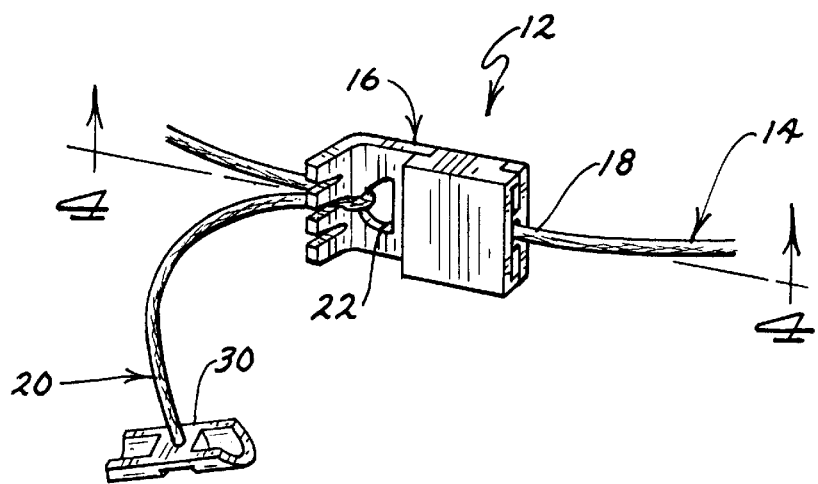
FIG. 2 is an enlarged perspective view of the cinch clip shown in FIG. 1, particularly illustrating the cord having been pulled down into one of the cord gripping recesses of the toothed locking member.

Cinch clip 12 comprises two cooperating components comprising a cord 14 and a toothed locking member 16. Referring to FIG. 2, a first end 18 of cord 14 is fixedly secured to locking member 16. Cord 14 then forms a loop 15 relative to locking member 16. A second end 20 of cord 14 is threaded back through an opening 22 in locking member 16.

Locking member 16 is provided with a row of upstanding teeth 24. Tapered cord receiving slots 26 are defined between adjacent teeth 24. Slots 26 are wider at the top of teeth 24 and narrower at the base of teeth 24 as shown most clearly in FIG. 3. Referring to FIG. 2, when cord 14 is pulled downwardly into one slot 26, the narrowing of slot 26 will tightly grip cord 14 after cord 14 is pulled down into slot 26 far enough.

Figure 3:
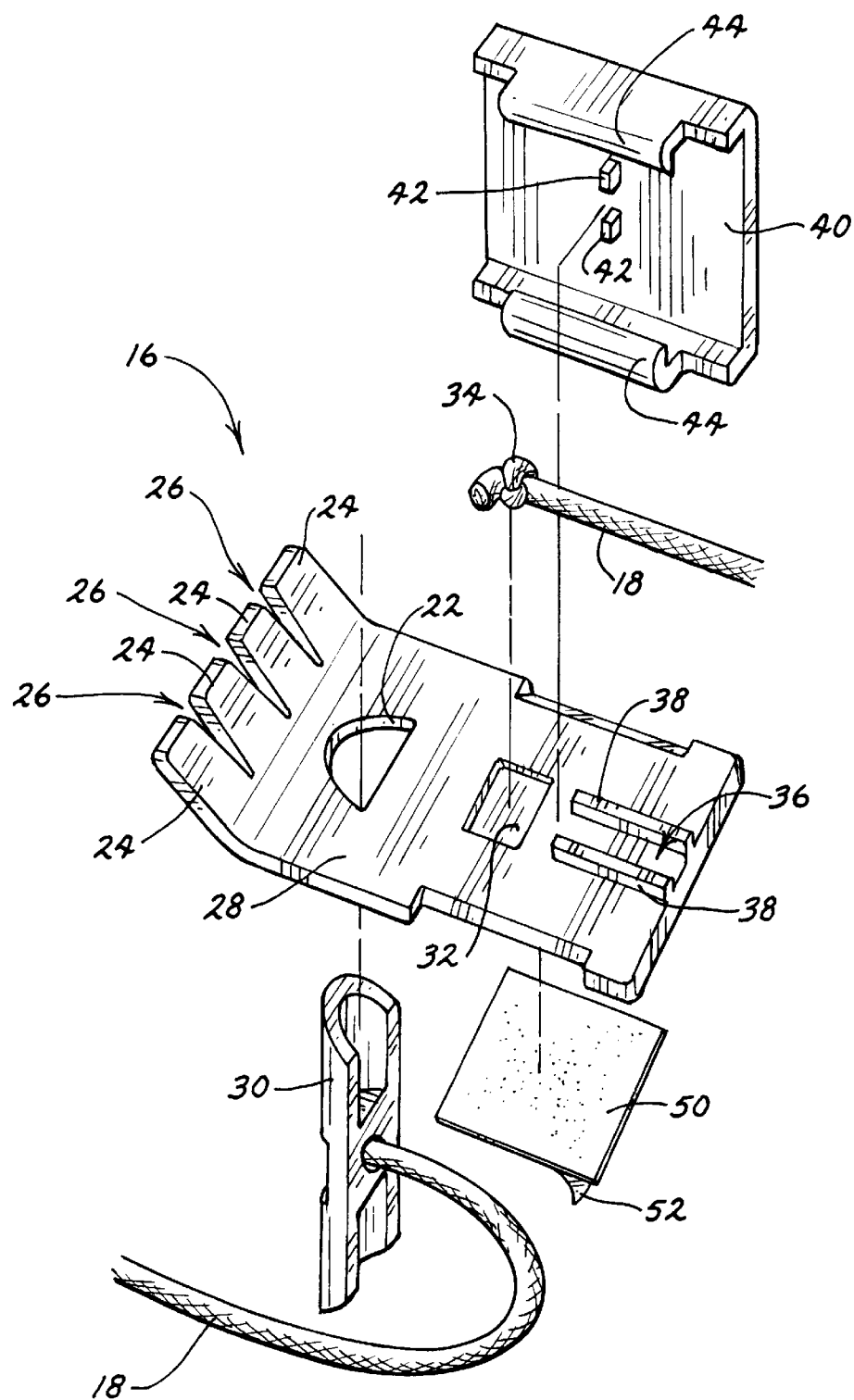
FIG. 3 is an exploded perspective view of the cinch clip shown in FIG. 1.

FIGS. 3–5 illustrate the construction of cinch clip 12. Referring first to FIG. 3, locking member 16 includes a base plate 28 on which teeth 24 are integrally formed. Teeth 24 extend upwardly from base plate 28 at an angle relative to base plate 28. As shown in FIG. 3, there are four teeth 24 which define three cord receiving slots 26. However, the number of teeth 24 and slots 26 could be varied. For example, only two teeth 24 defining only a single cord receiving slot 26 could be provided on base plate 28.

Opening 22 is provided in base plate 28 adjacent the row of teeth 24. Opening 22 is arch shaped to match, but be slightly larger than, an arch shaped cross-section of a handle 30 on second end 20 of cord 14. This permits handle 30 to be placed on end and threaded through opening 22 with the arch shaped cross-section of handle 30 passing up through the similar arch-shape of opening 22. Handle 30 permits the user to more easily grip second end 20 of cord 14 when tightening or cinching cord 14.

Base plate 28 of locking member 16 further includes a recess 32 in which a knot 34 on first end 18 of cord 14 is placed. Cord 14 then extends out over base plate 28 through a channel 36 formed by two upstanding walls 38 on base plate 28. Knot 34 on first end 18 of cord 14 is placed in recess 32 and cord 14 is laid within channel 36. After this is done, a retainer 40 is snapped down over base plate 28.

Retainer 40 includes downwardly extending tabs 42 which extend down so that one tab 42 is on each side of cord 14 to pinch cord 14 therebetween. In addition, retainer 40 includes curved, inturned flanges 44 that have a snap fit with each side of base plate 28. When retainer 40is snapped onto base plate 28 with first end 18 of cord 14 having first been placed into recess 32 of base plate 28, first end 18 of cord 14 is then securely fixed within locking member 16 with first end 18 of cord 14 not being able to slip out of locking member 16 due to its capture within recess 32 and between tabs 42 and its retention therein by retainer 40.

The above described method of securing first end 18 of cord 14 to locking member 16 allows locking member 16 to be manufactured and assembled without using tools. However, other ways of fixedly securing first end 18 of cord 14 to locking member 16 could obviously be used. For example, first end 18 of cord 14 could be adhesively secured to locking member 16 if so desired. All that is required is that first end 18 of cord 14 be fixedly secured to locking member 16 so that first end 18 of cord 14 does not pull out of locking member 16 during use of cinch clip 12.

The operation which threads second end 20 of cord 14 through opening 22 comprises aligning the arch shaped cross-section of handle 30 on second end 20 of cord 14 with opening 22 and then pushing handle 30 with the attached second end 20 of cord 14 up through opening 22 as indicated by the arrow A in FIG. 3. This threading operation is preferably done during manufacture of cinch clip 12 and not by the user. Preferably, cinch clip 12 when sold will have second end 20 of cord 14 already threaded through opening 22. Thus, cord 14 simply forms a loop relative to locking member 16 when the user picks up cinch clip 12.

Once handle 30 is passed through opening 22, handle 30 will be free to then extend laterally relative to opening 22 or to move into some other non-aligned position relative to opening 22. Thus, once the threading operation has been completed during manufacture of cinch clip 12, handle 30 actually prevents second end 20 of cord 14 from slipping back through opening 22. It would take a very conscious and deliberate act to realign the arch shaped cross-section of handle 30 with opening 22 to push handle 30 back through opening 22. Consequently, cinch clip 12 prior to use by the user would normally be provided with cord 14 forming a loop relative to locking member 16 and with second end 20 of cord 14 already threaded through opening 22 in base plate 28 of locking member 16.

Preferably, the various structural components of locking member 16 and handle 30 on second end 20 of cord 14 are molded from plastic. Cord 14 is preferably an elastic cord capable of being stretched or elongated up to about 50% from its usual, untensioned length. In other words, if cord 14 has a length of 6 inches when it is not under tension, cord 14 can elongate to approximately 9 inches when the user exerts a strong pull on second end 20 of cord 14 by pulling on handle 30. This elongation allows cord 14 to be wrapped or cinched tightly around the limb of the user, but also provides more comfort for the user after cord 14 is cinched.

Finally, locking member 16 is provided with an adhesive patch 50 on the underside of base plate 28. Adhesive patch 50 is normally covered by a protective backing 52. When protective backing 52 is peeled off by the user, locking member 16 can be secured or attached to the item that one desirably wishes to secure to or around the limb of the user. Adhesive patches 50 of this type with removable protective backings 52 are well known. FIG. 3 shows protective backing 52 with one corner thereof having been peeled down.

In using cinch clip 12 of this invention with a cast or bandage protector 2 in the form of a plastic bag 4, bag 4 is first slipped over the user's limb to cover the cast or bandage 6. This is shown in FIG. 1 with bag 4 being slipped over arm 8 of the user until open mouth 10 of bag 4 is located above the top of cast or bandage 6. Then, the user slips cinch clip 12 up over bag 4 by slipping loop 15 in cord 14 concentrically up over bag 4. Since cord 14 is elastic, loop 15 can be stretched out if necessary to pass up over bag 4. Cinch clip 12 is slipped up over bag 4 until cinch clip 12 is located near the top of bag 4 at a position where it will be effective to cinch or close mouth 10 of bag.

When cinch clip 12 has been positioned up over bag 4 at a desired location as shown in FIG. 1, protective backing 52 is peeled off the underside of adhesive patch 50, i.e. on the side of locking member 16. After protective backing 52 is peeled off, adhesive patch 50 on locking member 16 is simply pressed against the outside of bag 4 to adhesively attach locking member 16 to bag 4. After this has been done, the user can grab handle 30 on second end 20 of cord 14 and pull on cord 14 to cinch cord 14, and thus underlying bag 4, tightly around the user's arm 8. Obviously, if cord 14 is engaged within a slot 26 before the cinching operation takes place, the user first disengages cord 14 from slot 26 to permit cord 14 to be further drawn up through opening 22 and cinched. In any event, once cord 14 is cinched tightly around the user's arm 8, the user then simply pulls cord 14 downwardly into any slot 26 to grip and lock cord 14 in place.

After cord 14 has been cinched a first time in locking member 16, a portion of cord, as indicated at 60 in FIG. 1, will dangle downwardly from locking member 16. If cinch clip 12 has being cinched around a small enough limb, such as a wrist or an arm 8 of a small person, this dangling portion 60 of cord 14 may be long enough to permit cord 14 to be wrapped a second time around the limb of the user and then cinched again in another slot 26 on locking member 16. This further secures cord 14 in place. Accordingly, while locking member 16 could be provided with only a single cord receiving slot 26, it is preferred that locking member 16 have a plurality of such slots 26 to allow, in appropriate cases, multiple passes of cord 14 around the user's limb and multiple cinches of cord 14 within different slots 26 of locking member 16.

Cinch clip 12 of this invention allows a cast or bandage protector 2 to be quickly and easily installed over a cast or bandage 6 on a user's limb. It is simple and easy to cinch cord 14 around the user's limb even using just one hand of the user. Moreover, once tightened, it is comfortable. Finally, it is inexpensive such that the entire cast or bandage protector 2 with cinch clip 12 can be discarded after a single use.

Cinch clip 12 of this invention would have uses other than simply cinching a cast or bandage protector 2 in place on a user's limb. For example, it could be used to hold a sterile dressing over a wound. For example, two cinch clips 12 could be used on the dressing, one at the top of the dressing above the wound and one at the bottom of the dressing beneath the wound. Moreover, it would also be useful to cinch any item that one might desirably wish to secure or hold on the limb of a user. For example, a cinch clip 12 of the type disclosed herein could be used to hold up a person's socks or to close off a sleeve opening around a person's wrists. Thus, while one use of cinch clip 12 of this invention is in connection with a cast or bandage protector 2, cinch clip 12 is not limited to this use.

Various modifications of this invention will be apparent to those skilled in the art. For example, while it is preferred that cord 14 be elastic to have some degree of stretchability, this need not be the case. Cord 14 could be non-elastic.

Moreover, prior to use, cinch clip 12 is preferably separate from cast or bandage protector 2. Cinch clip 12 is secured to cast or bandage protector 2 by the end user using adhesive patch 50 only after cinch clip 12 is first positioned around cast or bandage protector 2. This allows the user to position cinch clip 12 at the most preferred location on cast or bandage protector 2, i.e. slightly above the top of cast or bandage 6, prior to securing cinch clip 12 to cast or bandage protector 2. However, cinch clip 12 could be preassembled on cast or bandage protector 2. In this case, locking member 16 would be already adhered to cast or bandage protector 2 prior to use by the user if so desired. Thus, the scope of the invention shall be limited only by the appended claims.

I claim:

1. A cast or bandage protector for covering an arm or leg of a user, which comprises:
    (a) an elongated, flexible, plastic bag having an open end into which the arm or leg of the user can be inserted until the arm or leg is contained at least partly within the bag during use;
    (b) a cinch clip carried adjacent the open end of the bag for cinching the open end of the bag shut against the arm or leg of the user, wherein the cinch clip comprises:
        (i) a locking member comprising a substantially rigid base plate having an upper side and an underside, wherein the base plate is fixedly attached to the bag by an adhesive patch on a portion of the underside of the base plate, wherein the base plate further includes an opening passing therethrough between the upper side and the underside of the base plate with the opening being located in a portion of the base plate that is not covered by the adhesive patch;
        (ii) an elongated, flexible cord having a first end fixedly attached to the base plate of the locking member and a free second end that is threaded through the opening in the base plate of the locking member with the cord forming a loop relative to the locking member between the first and second ends thereof and with the loop adapted to be placed around the arm or leg of the user; and
    (c) a slot on the base plate of the locking member, said slot having an open end to allow the cord to be pulled into the slot through the open end thereof, wherein the slot has opposed sides which are configured for releasably gripping opposite sides of the cord after the second end of the cord has been pulled through the opening to tighten the cord loop around the limb of the user and after the cord has then been inserted into and pulled in-wardly into to the slot to thereby cinch and tighten the open end of the bag to the limb of the user.

2. The cast or bandage protector of claim 1, wherein the locking member is attached to the bag by the user after the user positions the locking member at a desired location on the bag.

3. The cast or bandage protector of claim 1, wherein the adhesive patch on the underside of the base plate is covered by a protective backing, and wherein the protective backing may be peeled off by the user to expose the adhesive patch to stick the locking member to the bag.

4. The cast or bandage protector of claim 1, wherein the slot on the locking member narrows from top to bottom such that the slot grips the cord as the cord is pulled downwardly into the slot.

5. The cast or bandage protector of claim 4, further including a plurality of the slots on the locking member.

6. The cast or bandage protector of claim 1, wherein the cord is an elastic cord.

7. The cast or bandage protector of claim 1, wherein the slot extends upwardly from the base plate with the open end of the slot facing upwardly relative to the base plate.

8. The cast or bandage protector of claim 7, wherein the slot extends upwardly at an angle relative to the base plate.

9. The cast or bandage protector of claim 1, wherein the second end of the cord includes a handle for allowing the second end of the cord to be more easily gripped and pulled, and wherein the handle and the opening in the base plate have sizes and cross-sectional shapes which are selected to allow the handle and the second end of the cord to be threaded through the opening from the underside of the base plate.

10. The cast or bandage protector of claim 9, wherein the cross-sectional shapes of the handle and the opening are the same but with the cross-sectional shape of the opening being slightly larger than the cross-sectional shape of the handle to permit the handle to pass through the opening when the handle is placed on end and pushed through the opening.

11. The cast or bandage protector of claim 1, wherein the first end of the cord has a knot which is fixedly secured in a recess on the base plate.

12. The cast or bandage protector or claim 11, wherein the knot on the first end of the cord is retained in the recess by a retainer which is secured to the base plate.

13. The cast or bandage protector of claim 12, wherein the retainer is snap fit to the base plate.

14. The cast or bandage protector of claim 12, wherein the retainer includes a pair of spaced tabs which pinch the first end of the cord against the base plate to help retain the first end of the cord on the base plate.

15. A cast or bandage protector for covering an arm or leg of a user, which comprises:
    (a) an elongated, flexible, plastic bag having an open end into which the arm or leg of the user can be inserted until the arm or leg is contained at least partly within the bag during use;
    (b) a cinch clip carried adjacent the open and of the bag for cinching the open end of the bag shut against the arm or leg of the user, wherein the cinch clip comprises:
        (i) a locking member attached to the bag, wherein the locking member includes a base plate and a retainer affixed to the base plate;

(ii) a cord having a first end fixedly attached to the locking member by clamping the first end of the cord between the base plate and the retainer, and wherein the cord includes a free second end that is threaded through an opening in the base plate of the locking member with the cord forming a loop relative to the locking member between the first and second ends thereof and with the loop adapted to be placed around the arm or leg of the user; and (c) a slot on the base plate of the locking member said slot having an open end to allow the cord to be pulled into the slot through the open end thereof, wherein the slot has opposed sides which are configured for releasably gripping opposite sides of the cord after the second end of the cord has been pulled through the opening to tighten the cord loop around the limb of the user and after the cord has then been inserted into and pulled inwardly into to the slot to thereby cinch and tighten the open end of the bag to the limb of the user.

16. The cast or bandage protector of claim 15, further including a plurality of slots on the locking member.

17. The cast or bandage protector of claim 16, wherein the slots extend upwardly from the base plate.

18. The cast or bandage protector of claim 16, wherein the slots extend upwardly at an angle from the base plate.

19. The cast or bandage protector of claim 15, wherein the opening is provided in the base plate to one side of the retainer.

* * * * *